United States Patent [19]

Foguet et al.

[11] Patent Number: 5,561,135
[45] Date of Patent: Oct. 1, 1996

[54] N,N,N',N'-TETRASUBSTITUTED-1,2-ETHANEDIAMINE DERIVATIVE COMPOUNDS

[75] Inventors: Rafael Foguet; Santiago Gubert; José Ortiz; Aurelio Sacristàn; Josep M. Castelló, all of Barcelona,, Spain

[73] Assignee: Ferrer Internacional, S.A., Barcelona, Spain

[21] Appl. No.: 392,987

[22] PCT Filed: Jul. 18, 1994

[86] PCT No.: PCT/EP94/02363

§ 371 Date: Apr. 21, 1995

§ 102(e) Date: Apr. 21, 1995

[87] PCT Pub. No.: WO95/03270

PCT Pub. Date: Feb. 2, 1995

[30] Foreign Application Priority Data

Jul. 19, 1993 [ES] Spain ...................... 9301616

[51] Int. Cl.[6] ............... A61K 31/135; A61K 31/505; C07C 215/30; C07D 239/42

[52] U.S. Cl. .................... 514/275; 514/648; 514/649; 514/653; 544/297; 564/316; 564/343; 564/345; 564/355

[58] Field of Search .............. 544/297; 564/316, 564/343, 345, 355; 514/275, 648, 649, 653

[56] References Cited

U.S. PATENT DOCUMENTS

| | | | |
|---|---|---|---|
| 3,794,645 | 2/1974 | Pieper et al. | 260/239 B |
| 4,588,728 | 5/1986 | Ferris | 514/255 |
| 4,709,094 | 11/1987 | Weber et al. | 564/238 |
| 4,929,734 | 5/1990 | Coughenour et al. | 546/338 |
| 4,988,735 | 1/1991 | Casagrande et al. | 514/648 |
| 5,061,728 | 10/1991 | Koe | 514/520 |
| 5,086,054 | 2/1992 | Parish | 514/239.2 |
| 5,109,002 | 4/1992 | Cain et al. | 514/256 |
| 5,116,995 | 5/1992 | Nakazato et al. | 548/444 |
| 5,149,817 | 2/1992 | Matsumura et al. | 546/281 |
| 5,158,947 | 10/1992 | Tatsuoka et al. | 514/211 |
| 5,162,341 | 11/1992 | Cook | 514/317 |
| 5,175,174 | 12/1992 | Lubisch et al. | 514/318 |

FOREIGN PATENT DOCUMENTS 2279383  2/1976  France .

*Primary Examiner*—Richard L. Raymond
*Attorney, Agent, or Firm*—Birch, Stewart, Kolasch & Birch, LLP

[57] ABSTRACT

The invention relates to new N,N,N'N'-tetra-substituted-1,2-ethanediamine compounds of the general formula (I):

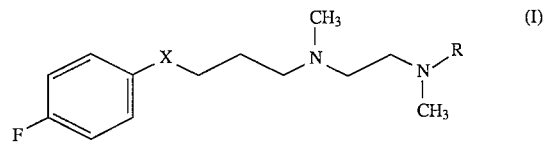

wherein X is a carbonyl (CO), hydroxymethylen (CHOH) or p-fluorophenyl-methylen (p—F—$C_6H_4$—CH) group and R is a benzyl group optionally substituted in p— with an halogen, or R is a 2-pyrimidinyl group with the proviso that simultaneously X may not be p-fluorophenyl-methylen (p—F—$C_6H_4$—CH) and R may not be an unsubstituted benzyl group, as well as their pharmaceutically acceptable additions salts.

The compounds are potentially useful in the treatment of sigma receptor-related nervous system diseases.

8 Claims, No Drawings

N,N,N',N'-TETRASUBSTITUTED-1,2-ETHANEDIAMINE DERIVATIVE COMPOUNDS

This application is a 371 of PCT/EP94/02363, filed Jul. 18, 1994.

DESCRIPTION

The present invention relates to new N,N,N'N'-tetrasubstituted-1,2-ethanediamine compounds of the general formula (I):

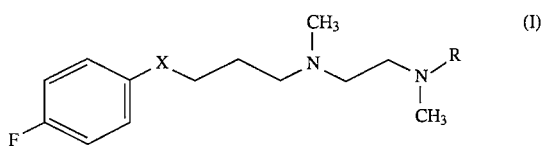

wherein X is a carbonyl (CO), hydroxymethylen (CHOH) or p-fluorophenyl-methylen (p—F—$C_6H_4$—CH) group and R is a benzyl group optionally substituted in p- with an halogen, or R is a 2-pyrimidinyl group with the proviso that simultaneously X may not be p-fluorophenyl-methylen (p—F—$C_6H_4$—CH) and R may not be an unsubstituted benzyl group, as well as their pharmaceutically acceptable additions salts.

In the compounds of the general formula (I), the halogen that optionally substitutes the benzyl group p-position is preferably fluorine. Among the pharmaceutically acceptable salts, hydrochlorides and sulfates are preferred.

The compounds of the present invention are obtained according

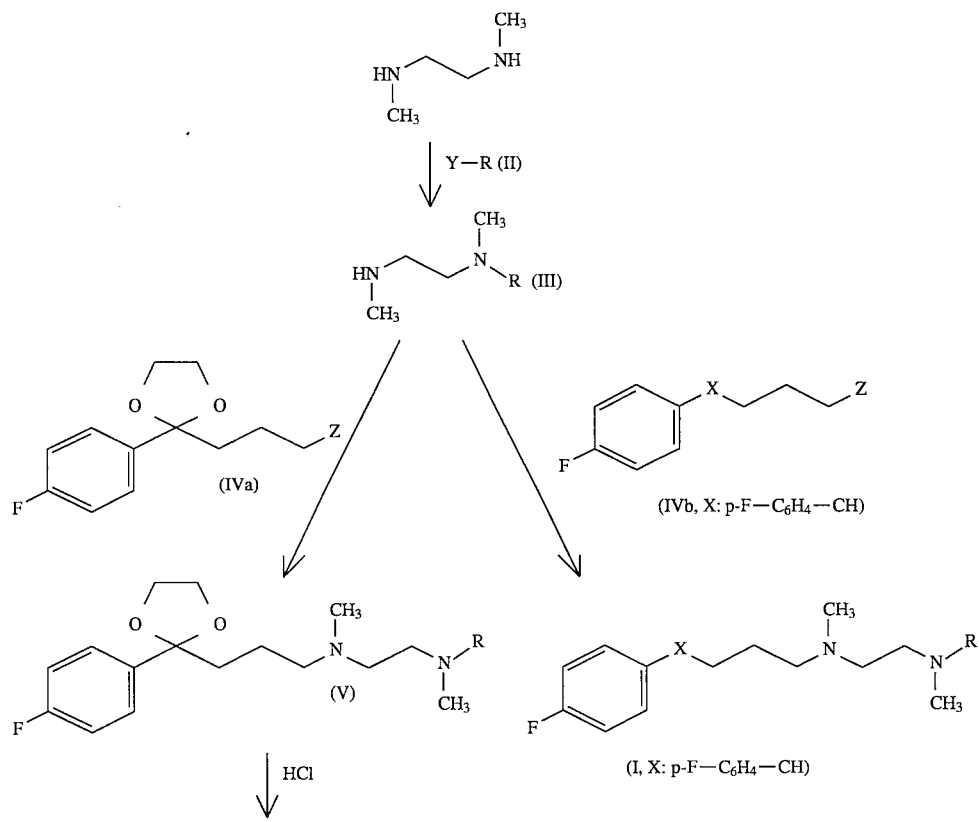

-continued
Scheme 1

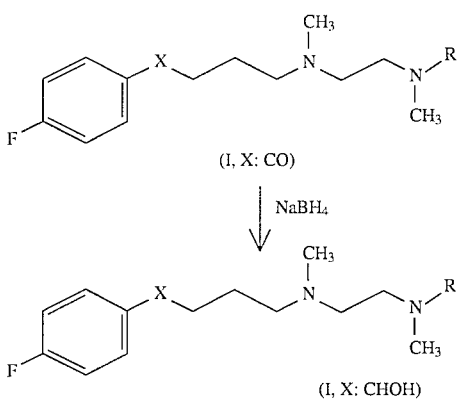

(I, X: CO)

↓ NaBH₄

(I, X: CHOH)

In effect, the alkylation of N,N'-dimethyl-1,2-ethanediamine with a halogenide of the general formula (II), wherein Y is chlorine or bromine and R is as defined in (I) leads to the intermediates of the general formula (III) wherein R is as defined in (I). Applicants have found out that the use of chlorinated compounds (II, Y=Cl) is advantageous for alkylation reactions. Thus, preferred compounds of the general formula (II) for use in this reaction include benzyl chloride, p-fluorobenzyl chloride, 2- chloropyrimidine and the like.

Subsequent alkylation of the intermediates of general formula (III) with 2-(4-fluorophenyl)-2-(3-halopropyl)-1,3-dioxolane (IVa), wherein Z is preferably chlorine, leads to the intermediates of general formula (V), 1,3-dioxolane derivatives. This reaction occurs conveniently in the presence of a base that reacts with the hydracid formed, Applicants have found out that carbonate- and acid carbonate-like mineral bases, such as potassium carbonate, are extremely appropriate for this reaction. It is also convenient the addition of a catalytic amount of potassium iodide in order to accelerate the reaction course. Usually, acetonitrile-like inert solvent is recommended as reaction medium. The reaction occurs in the presence of heat, preferably at the boiling temperature of the mixture.

Acid hydrolysis of 1,3-dioxolanes (V) provides the final compounds of general formula (I) of this invention, wherein X is carbonyl (CO) and R is defined as aforesaid. This reaction occurs conveniently in a hydroalcohol medium, which preferably includes a mixture of water and an alkanol having four carbon atoms at most, preferably ethanol. A mineral acid is selected as choice acid, such as hydrochloric acid, hydrobromic acid and the like.

The compounds (I, X=CO) obtained as described in the preceding paragraph provide by reduction the final compounds of general formula (I), wherein X is hydroxymethylen (CHOH) and R is as defined. The reduction is conveniently carried out using a hydride-like reductor such as sodium borohydride, and in an anhydrous alkanol medium such as absolute ethanol.

Unlike the final products (I) when X is a carbonyl group (CO), the final products (I) when X is p-fluorophenylmethylene (p—F—C₆H₄—CH) are obtained from the intermediates of general formula (III) by a single-step reaction. This reaction is carried out with an alkylating agent selected from a 1,1'-(4-halobutyliden)bis(4-fluorobenzene) (IVb). This alkylation is essentially similar to that performed with (IVa) and is carried out in the presence of the same coadjuvants and solvents. In (IVb), the Z halogen atom has the same nature as in (IVa).

U.S. Pat. No. 4588728 describes the treatment of psychosis with cis-9- [3- (3,5-dimethylpiperazinyl)propyl] carbazole. U.S. Pat. No. 4709094 describes the preparation of 1,3-disubstituted guanidines as well as their utility in the diagnosis and treatment of hallucinations associated with psychotic disorders and chronic mental depression. U.S. Pat. No. 4929734 describes the preparation of N-substituted 1-(1,2,3,6-tetrahydro-3-piridinyl)oximes and N-substituted 1(1,2,3,6-tetrahydro-4-piridinyl)oximes and their use in treating depression, psychosis and/or inflammatory diseases. U.S. Pat. No. 5061728 describes the use of 4-phenyl-1,2,3,4-tetrahydro-1-naphthalenamine derivatives in treating psychosis and inflammation and their use as immunosupressants. U.S. Pat. No. 5086054 describes the preparation of arylcycloalkylpolyalkyl-amines and their use as antipsychotic, anti-ischemic, anti-apoplectic, anti-dementia agents and anticonvulsants. U.S. Pat. No. 5162341 describes the use of various compounds for combating amphetamine and analogous drug abuse. U.S. Pat. No. 5175174 describes the preparation of N-phenyl-piperidyl-4-amine derivatives and their use as Class III antiarrhythmic agents, potassium channel blockers, antipsychotics, anticonvulsants and neuroprotectors. U.S. Pat. No. 5158947 describes the preparation of N-piperidyl-alkyl-benzazepine derivatives and their utility for the treatment of psychoneurosis. U.S. Pat. No. 5116995 describes the preparation of 4-(aminoalkyl)-carbazole and their use as antipsychotics. U.S. Pat. No. 5149817 describes the preparation of 4-phenyl- and 4-thienyltetrahydropyridine and their use for treating depression, mania, schizophrenia and cerebral ischemia. U.S. Pat. No. 5109002 discloses 1-cycloalkyl-piperidine derivatives and their use as antipsychotics and for treating dyskinesia.

The compounds disclosed in all these patents share their affinity as ligands for sigma (σ) receptors of nervous system. To this regard, literature reviews by B. L. Largent et al ("Eur J. Pharmacol" 155 345-7, 1988) S. I. Deutsch et al ("Clinical Neuropharmacology", 11(2), 105–119, 1988) and T. P. Su ("Eur. J. Blochem.", 200, 633–642, 1991) are illustrative of the biochemical, pharmacological and clinical aspects of sigma-receptor ligands.

Applicants have found out that although the compounds of the present invention are chemically very different from those of the above prior art patents, they show a high affinity as ligands for sigma receptors. Due to such an activity, they are potentially useful in the treatment of some sigma receptor-related mental disorders, mainly psychosis and schizophrenia.

Moreover, from patent literature there are known 1,2-ethanediamine derivative compounds having several N-atom substitutions, and where substituents are structurally similar to those in the compounds of general formula (I). For instance, FR Patent No. 2279383 discloses, among other compounds, N-benzyl-N'-(4,4-bis-(4-fluorophenyl)butyl)-N, N'-dimethyl-1,2-ethanediamine, the only difference from the compound of Example 9 in this invention being a p-position fluorine atom of the benzyl group. However, N-benzyl-N'-(4,4-bis-(4-fluorophenyl)butyl)-N,N'-dimethyl-1,2-ethanediamine in the aforesaid French patent is simply an intermediate, which is used to obtain compounds having cardiovascular activity. Similarly, U.S. Pat. No. 3794645 discloses, among other compounds, 4-amino-3,5-dibromo-α-[3- [[2- (diethylamino) ethyl]amino]propyl]-4'-fluorobenzhydrol belonging to a group of compounds reported to have sedative, antiemetic and inhibitory activity in stomach ulcer, and be useful as central nervous system stimulants. This compound is structurally rather similar to the compounds in Examples 6, 8 and 9. Similarly, EP Patent No. 511072 discloses, among other compounds, 2-[[2-[[3-(4-fluorophenoxy)propyl]methylamino]ethyl]amino]-4-pyrimidine-carboxamide belonging to a group of compounds that have an antagonist action on $\alpha_1$-adrenergic receptor and potentially useful in treating disorders caused by $\alpha_1$-adrenergic hyperactivity in the low urinary tract, especially benign hypertrophy of prostate, dysuria and polyuria. This compound is structurally rather similar to the compounds in Examples 12 and 13.

Despite the structural similarities between the compounds of general formula (I) and the aforesaid compounds described in patent literature, applicants have found out that the compounds of general formula (I) are surprisingly able to be bound to σ receptors and, consequently, they are potentially useful in treating σ receptor-related diseases. Haloperidol is widely used in therapy as an antipsychotic agent that acts on both σ and $D_2$ receptors (B. L. Largent et al, "Eur. J. Pharmacol.", 155, 345-7, 1988). In contrast, the compounds of this invention show as a main advantage over Haloperidol their high selectivity on σ receptors versus $D_2$ receptors, which results in a lesser possibility of developing extrapyramidal effects on account of the interaction with $D_2$ receptors (Table 1). The results in Table 1 show that the preferred compound in the present invention is 1-(p-fluorophenyl)-4-[N-(2-(N'-(p-fluorobenzyl)-N'-methyl-amino) ethyl)-N-methylamino]-1-butanone dihydrochloride (I, X: CO, R: p—F—$C_6H_4$—$CH_2$—, 2HCl, Example 7) because it is more potent than Haloperidol due to its potential binding to σ receptors and, in addition, poorly active on $D_2$ receptors. Furthermore, the lower incidence of side-effects in the compound of Ex. 7 with regard to Haloperidol has been made evident by means of the stereotypy inhibition test (Table 2 ) and Irwin test (Table 3 ).

Specific binding to σ and $D_2$ receptors has been tested as follows:

σ receptors: A 2-nM solution of radioactive 3-PPP ((+) [$^3$H]3-[3-hydroxyphenyl]-N-(1-propyl)-piperidine), which acts as a specific ligand, was incubated with the membrane corresponding to 40 mg of guinea-pig total brain for 90 min at 25° C. buffered at pH 8.5 with Tris.HCl. Thus, total binding of ligand to membranes was attained. Non-specific binding was then determined by adding a micromolar concentration of unlabelled 3-PPP. $IC_{50}$ values (inhibitory concentration 50%) were calculated from the inhibition rate of the specific binding obtained by adding eleven different concentrations of the compounds to be tested. After the incubation was completed, the samples were filtered through a glass fiber filter and then washed three times with Tris.HCl buffer. The amount of receptor-bound radioactivity was retained on the membrane and determined by liquid scintillation counting.

$D_2$ receptors: A 2-nM solution of radioactive spiperone ([$^3$H]spiperone), which acts as a specific ligand, was incubated with the membrane corresponding to 20 mg of rat striatum for 20 min at 35° C. buffered at pH 7.4 with Tris.HCl. The non-specific binding was then determined by addition of a micromolar concentration of unlabelled spiperone. $IC_{50}$ (inhibitory concentration 50%) was calculated from the inhibition rate of the specific binding obtained by addition of eleven different concentrations of the compounds to be tested. After the incubation was completed, the sample were filtered through a glass fiber filter and then washed three times with Tris.HCl buffer. The amount of receptor-bound radioactivity was retained on the membrane and determined by liquid scintillation counting.

Stereotypy inhibition test: Male Sprague-Dawley rats, weighing 200–300 g were used. The animals were weighed and then placed in individual transparent boxes. At time 0 the compounds to be tested were administered intraperitoneally. 0.25% agar was used as vehicle. After 30 min, apomorphine was injected subcutaneously at a dose of 1.5 mg/kg in a concentration of 0.6 mg/ml. At 40, 50, 60, 90 and 120 min, stereotypy was scored from (–) to (+++) according to the following criteria: (–) absence of stereotypy or any abnormal movement; (+) presence of slight stereotyped movements of the head and intermittent sniffing; (++) intense movements of the head, mild licking interspersed with sniffing; and (+++) intense licking and/or gnawing. Results are expressed as $ED_{50}$ in mg/kg for a better quantification.

Irwin test: It consists in a package of tests intended to find out the properties of a compound as well as the magnitude of such properties which are completely unknown. Assessment begins with general observations until reaching gradually more detailed observations. Changes are arbitrarily scored from the observations of control animals.

On the basis of animals' behaviour, the following parameters were assessed:

a) General examination: sex, weight, age, . . .

b) Behavioural examination: alertness, locomotor activity, mood.

c) Neurological examination: central nervous system, autonomic nervous system, body carriage, motor incoordination, muscular tone, reflexes and general signs.

The results have been expressed as the first dose causing behavioural and neurological undesirable effects. Under the experimental conditions described, $IC_{50}$ values on σ and $D_2$ receptors expressed in nanomolar concentrations (nM) are shown in Table 1. This table also contains the $D_2$/σ ratio of selectivity and the $D_2$/σ ratio of relative selectivity to Haloperidol. Thus, preferred compounds are those whose $D_2$/σ ratio of selectivity is higher. Haloperidol is less selective.

TABLE 1

| Compound | $IC_{50}$ (nM) | | Selectivity | |
|---|---|---|---|---|
| | σ | $D_2$ | $D_2$/σ | Relative selectivity |
| Ex. 5 | 2.01 | 410 | 204 | 42.5 |
| Ex. 6 | 29.0 | 81800 | 2821 | 587.7 |
| Ex. 7 | 0.52 | 678 | 1304 | 271.7 |
| Ex. 8 | 2.79 | 7810 | 2799 | 583.1 |
| Ex. 9 | 83.0 | 2350 | 28 | 5.8 |
| Ex. 12 | 14.6 | 1500 | 103 | 21.5 |
| HPL* | 1.62 | 7.73 | 4.8 | 1 |

*Haloperidol

In Table 2, the results on stereotypy, expressed as $ED_{50}$ (mg/Kg), show that the $ED_{50}$ of the compound in Ex. 7, 1-(p-fluorophenyl)-4-[N-(2-(N'-(p-fluorobenzyl)-N'-methylamino) ethyl)-N-methylamino]-1-butanone dihydrochloride, was 80 times higher than that for Haloperidol. This indicates that the novel compound is much less potent as inductor of undesirable abnormal movements attributed to $D_2$ receptors. This finding is, in addition, consistent with the biochemical results shown in Table 1.

Moreover, the results of Irwin test (Table 3) show that no undesirable effects were observed for 1-(p-fluorophenyl)-4 [N-(2-(N'-(p-fluorobenzyl)-N'-methylamino)ethyl-N-methylamino]-1-butanone dihydrochloride until the dose was 10 times higher than that for Haloperidol. The novel compound, unlike Haloperidol, does not produce catalepsy, which is its main therapeutic advantage.

TABLE 2

| Compound | $ED_{50}$ (mg/kg) |
| --- | --- |
| Example 7 | 32 |
| Haloperidol | 0.4 |

TABLE 3

| Compound | First dose (mg/kg) | Side effects |
| --- | --- | --- |
| Example 7 | 100 | Hypothermia, motor incoordination, decreased musuclar tone, decreased motor activity. |
| Haloperidol | 10 | Hypothermia, Catalepsy. |

The experimental results obtained suggest that the compounds of the invention can be useful in the treatment of sigma receptor-related nervous system diseases, and especially in anoxia, anxiety, convulsions, dyskinesia, drug addiction, schizophrenia, hypoxia, cerebral ischemia, mania, psychosis and stress. The compounds can be administered in combination with suitable vehicles via the oral, rectal or parenteral routes. These compounds are administered in doses ranging from 0.5 up to 100 mg per day, more preferably from 1 up to 30 mg per day.

EXAMPLE 1:

1-Benzyl-1,4-dimethyl-ethylenediamine

N,N'-dimethyl-ethylenediamine (88.15 g, 1 mole) was dissolved in absolute ethanol (300 ml). Then, $NaHCO_3$ (252 g, 3 mole), benzyl chloride (126.5 g, 1 mole) and ethanol to 1-l. volume were added. The mixture was refluxed for 20 h and then cooled. The inorganic salts were filtered, the solid was washed using small volumes of ethanol, and the liquid phase was evaporated until removal of all the ethanol. The pure product was recovered by high-vacuumdistillation (pressure: 0.1 mmHg, distillation temp.: 58°–60° C.) in the form of a light transparent, colourless oil. Yield: 51.1%.

EXAMPLE 2:

1,4 -Dimethyl -1-(p-fluorobenzyl)ethylenediamine

In the same manner as in Example 1 and using 4-fluorobenzyl chloride as the starting material, 1,4-dimethyl-1-(p-fluorobenzyl)ethylendiamine was obtained. Distillation temp.: 66°–67° C. at 0.01 mmHg pressure. Yield: 57.6%.

EXAMPLE 3:

4-[N-(2-(N'-benzyl,N'-methylamino)ethyl)-N-methylamino]-1-(p-fluorophenyl)-1-butanone ethyleneketal dihydrochloride A mixture of 1-benzyl-1,4-dimethyl-ethylenediamine (35.6 g, 0.2 mole), γ-chloro-p-fluorobutyrophenone-ethyleneketal (58.7 g, 0.24 mole), anhydrous $K_2CO_3$ (82.8 g, 0.6 mole) and a catalytic amount of KI in acetonitrile (500 ml) was stirred, heated under reflux for 24 hours and the reaction course was monitored by TLC ($Cl_3CH$—MeOH, 9:1; silica-gel $F_{254}$). The resulting solution was allowed to become temperate, the inorganic salts were filtered and the solvent was evaporated using a rotavapor. The liquid obtained was subjected to chromatographic purification (silica-gel; $Cl_3CH:MeOH$, 9:1). The fractions, which by TLC show the presence of pure product, were combined and the solvent was evaporated to afford 32.0 g (Yield, 50.5%) in the form of a light oil which was used as such in the following step.

IR (film) ν: 2960, 2800,1505, 1230 $cm^{-1}$.

$^1H$—NMR ($CDCl_3$) δ: 1.5–2.4 (m, 10H, —$CH_2$—), 2.20 (s, 3H, $CH_3$), 2.45 (s, 3H, $CH_3$), 3.5 (s, 2H, —$CH_2Ar$),

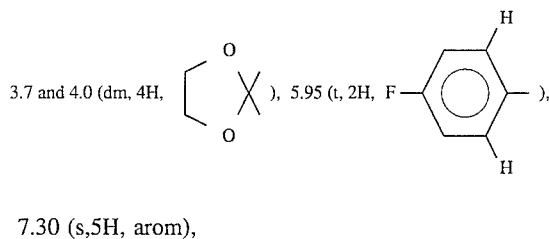

3.7 and 4.0 (dm, 4H,   ), 5.95 (t, 2H, F— ... —), 7.30 (s,5H, arom),

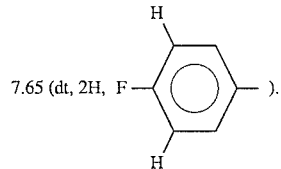

7.65 (dt, 2H, F— ... —).

2 basic groups: 94.1%.

EXAMPLE 4:

1-(p-fluorophenyl)-4-[N-(2-(N'-(p-fluorobenzyl)-N'-methylamino)ethyl)-N-methylamino]-1-butanone ethyleneketal dihydrochloride In the same manner as in Example 3, and using 1,4 -dimethyl-1-(4-fluorobenzyl) ethylenediamine as the starting material, the above-captioned compound was isolated to yield 43.6%.

IR (film) ν:2960, 2805, 1510, 1230 $cm^{-1}$.

$^1H$—NMR ($CDCl_3$) δ: 1.4–2.35 (m, 10H, —$CH_2$—), 2.20 (s, 3H, $CH_3$) , 2.47 (s, 3H, $CH_3$), 3.45 (s, 2H, —$CH_2Ar$),

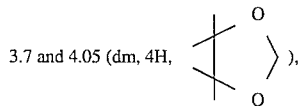

3.7 and 4.05 (dm, 4H,   ), 7.0 (dt, 4H, arom), 7.55 (m, 4H, arom).

2 basic groups: 94.7%.

EXAMPLE 5:

4-[N-(2-(N'-benzyl,N'-methylamino)ethyl)-N-methylamino]-1-(p-fluorophenyl)-1-butanone dihydrochloride Ethyleneketal from Example 3 (R=H) (38,6 g, 0,1 moles) was dissolved in absolute ethanol (300 ml), 100 ml of 6M HCl were added and the mixture was maintained at 60°–70°

C. for a period of 2 h. This period was proved by TLC to be sufficient for a total hydrolysis. Then, the ethanol was evaporated, and the oil obtained was crystallized in i-PrOH to give 22.3 g (Yield, 54%) of product.

IR (KBr) v: 3440, 2630, 2480, 1680, 1600, 1230 cm$^{-1}$.

$^1$H—NMR (D$_2$O) δ: 2.40 (m, 2H, NCH$_2$CH$_2$CH$_2$CO), 3.20 (s, 3H, CH$_3$), 3.30 (s, 3H, CH$_3$), 3.50 (m, 4H, NCH$_2$CH$_2$CH$_2$CO), 3.95 (s, 4H, NCH$_2$CH$_2$N), 4.75 (s, 2H, CH$_2$Ar),

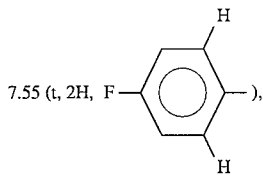

7.55 (t, 2H, F—⟨⟩—), 7.90 (s, 5H, Ar),

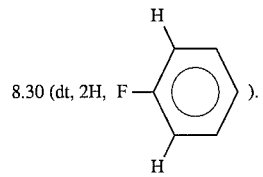

8.30 (dt, 2H, F—⟨⟩).

Melting point: 210°–215° C. (d).

2 basic groups: 97.8%.

Elemental analysis for C$_{21}$H$_{27}$FN$_2$O·2HCl: (found) C 60.56 H 6.94 N 6.52 Cl$^{31}$ 16.93; (calculated) C 60.42 H 7.04 N 6.74 Cl$^-$ 17, 07.

EXAMPLE 6:

4-[N-(2-(N'-benzyl, N'-methylamino)ethyl) -N-methylamino]-1-(p-fluorophenyl)-1-butanol dihydrochloride A mixture of the ketone obtained in Example 5 (8.3 g, 0,02 mole) and sodium borohydride (1.21 g, 0.032 mole) in absolute ethanol (700 ml) was allowed to react at room temperature with stirring for 18 h. The mixture was treated with ethanol 6M HCl (50 ml), stirred at room temperature for 2 h and then refluxed for 20 min. The solvent was removed in vacuo, the residual product obtained was treated with 2M NaOH (200 ml) and extracted with chloroform (3×200 ml). The organic phase separated was washed with water (200 ml ), dried over anhydrous Na$_2$SO$_4$ and concentrated in vacuo. There was obtained a resin which, after dissolving in isopropanol and treating with 6M EtOH-HCl, precipitated in the form of a crystalline white solid (6.2 g; yield, 74.3%) .

IR (KBr) v: 3400, 2640, 2480, 1520, 1230 cm$^{-1}$.

$^1$H—NMR (D$_2$O) δ: 2.1 (m, 4H, CHOH—CH$_2$—CH$_2$CH$_2$N), 3.20 (s, 6H, 2×CH$_3$), 3.5 (t, 2H, CH$_2$N), 3.90 (s, 4H, NCH$_2$CH$_2$N). 4.70 (s, 2H, CH$_2$Ar),

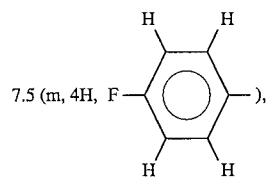

7.5 (m, 4H, F—⟨⟩—), 7.85 (s, 5H, Ar).

Melting point 208°–209° C. (d).

2 basic groups: 97.9%.

Elemental analysis for C$_{21}$H$_{29}$FN$_2$O·2HCl: (found) C 60.05 H 7.52 N 6.76 Cl$^-$16.90; (calculated) C 60.43 H 7.49 N 6.71 Cl$^-$16.98.

EXAMPLE 7:

1-(p-fluorophenyl)-4-[N-(2-(N'-(p-fluorobenzyl)-N'-methylamino)ethyl)-N-methylamino]-1-butanone dihydrochloride In the sample as in Example 5, and using the corresponding ethyleneketal as the starting material, the above-captioned compound is obtained (Yield, 83.1%).

IR (KBr) v: 3440, 2450, 1680, 1600, 1570, 1240 cm$^{-1}$.

$^1$H—NMR (D$_2$O) δ: 2.0 (m, 2H, NCH$_2$CH$_2$CH$_2$CO), 2.77 and 2.85 (s, 6H, 2×CH$_3$), 3.05 (t, 2H, COCH$_2$CH$_2$CH$_2$N), 3.2 (t, 2H, COCH$_2$CH$_2$CH$_2$N), 3.6 (s, 4H, NCH$_2$CH$_2$N), 4.3 (s, 2H, CH$_2$Ar),

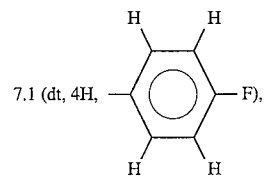

7.1 (dt, 4H, —⟨⟩—F),

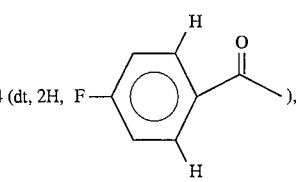

7.4 (dt, 2H, F—⟨⟩—),

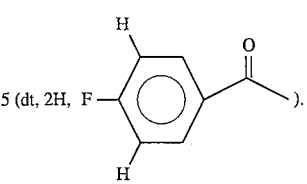

7.85 (dt, 2H, F—⟨⟩—).

Melting point: 227°–229° C. (d).

1 basic group: 98.48%.

Elemental analysis for C$_{21}$H$_{27}$F$_2$N$_2$O·2HCl: (found) C 58.03 H 6.33 N 6.38 Cl$^{-1}$ 16.40; (calculated) C 58.20 H 6.51 N 6.46 C$^-$16.36.

EXAMPLE 8:

1-(p-fluorophenyl)-4-[N-(2-(N'-(p-fluorobenzyl)-N'-methylamino)ethyl)-N-methanlamino]-1-butanol dihydrochloride In the same manner as in Example 6, and using the corresponding ketone as the starting material, the above-captioned compound was obtained (Yield, 87.9%).

IR (KBr) v: 3440, 2640, 2480, 1520, 1230 cm$^{-1}$.

$^1$H—NMR (D$_2$O) δ: 2,0 (m, 4H, NCH$_2$CH$_2$CH$_2$CHOH), 3.1 (s, 6H, 2×CH$_3$), 3.40 (t, 2H, NCH$_2$CH$_2$CH$_2$CHOH), 3.80 (s, 4H, NCH$_2$CH$_2$N), 4.65 (s, 2H, CH$_2$Ar), 7.5 (m, 8H, aromatic).

Melting point: 218°–222° C.

2 basic groups: 99.9%.

Elemental analysis for C$_{21}$H$_{28}$F$_2$N$_2$O·2HCl: (found) C 57.36 H 6.77 N 6.20 Cl$^-$15.92; (calculated) C 57.93 H 6.95 N 6.43 Cl$^-$16.20.

EXAMPLE 9:

N-(4,4-bis(p-fluorophnyl)butyl)-N,N'-dimethyl-N'-(p-fluorobenzyl)-1,2-ethanediamine dihydrochloride A mixture of the compound in Example 2 (19.6 g, 0.1 mole), 1,1'- (4-chloro-buthylden)bis(4-fluorobenzene) (3.65 g, 0.13 mole), anhydrous $K_2CO_3$ (41.4 g, 0.3 mole) and a catalytic amount of KI in acetonitrile (400 ml) was refluxed under stirring for a period of 18 h; the reaction was monitored by TLC (silica gel $F_{254}$, $Cl_3CH/MeOH$ 9:1). The reaction liquid was filtered and the solvent was evaporated. The oil obtained was purified by flash chromatography (silica gel, $Cl_3CH/MeOH$ 9:1) and crystallized as dihydrochloride by dissolving under heating with ethanol-HCl. 35.3 g (Yield, 68.8%) of a crystalline white product were obtained.

IR (KBr) v: 3440, 2925, 1510, 1240 cm$^{-1}$.

$^1$H—NMR (D$_2$O) δ:

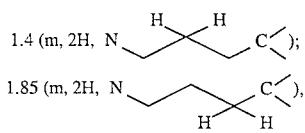

2.66–2.70 (2s, 6H, 2×CH$_3$),

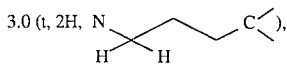

3.40 (s, 4H, NCH$_2$CH$_2$N), 3.75 (t, 1H, —CH), 4.2 (s, 2H, —CH$_2$Ar),

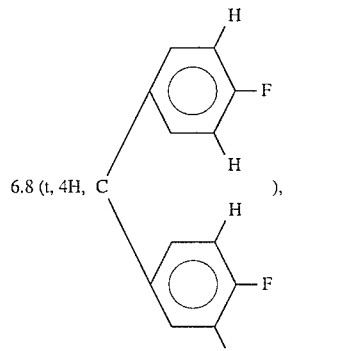

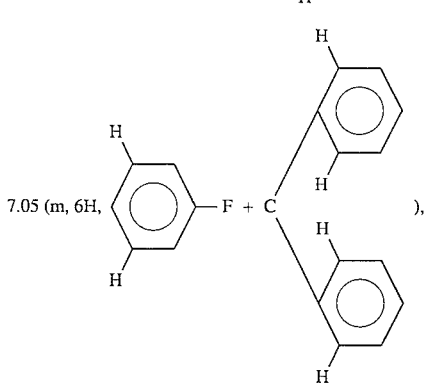

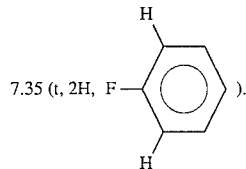

Melting point: 203°–206° C.

2 basic groups: 99.4%.

Elemental analysis for $C_{27}H_{31}F_3N_2$·2HCl: (found) C 63.07 H 6.47 N 5.34 Cl$^-$13.72; (calculated) C 63.16 H 6.48 N 5.46 Cl$^-$13.81.

EXAMPLE 10:

1,4-Dimethyl-1-(2-pyrimidinyl)ethylenediamine

A mixture of N,N'-dimethylethylenediamine (88.1 g, 1 mole), 2-chloropyrimidine (114.5 g, 1 mole), NaHCO$_3$ (252 g, 3 mole), in ethanol (1 litre) was stirred and heated under reflux for a period of 24 h. The solution was allowed to become temperate, then filtered in order to remove the inorganic salts, and the solvent was evaporated using a rotavapor. An oily liquid, which was dissolved in 500 ml of 1M HCl, was extracted two times with chloroform (2×250 ml). The aqueous phase was basified and extracted three times with chloroform (3×250 ml); the organic fractions were combined, dried over anhydrous Na$_2$SO$_4$, filtered, and the solvent was evaporated to give 54 g (Yield, 32.5%) of a chromatographically pure light oil, which was thus used in the following step.

IR (film) v: 3320, 2940, 1590, 1410, 1390 cm$^{-1}$.

$^1$H—NMR (CDCl$_3$) δ: 1.2 (s, 1H, NH), 2.45 and 3.20 (s, 6H, 2×CH$_3$), 2.8 (t, 2H, HN—CH$_2$CH$_2$N), 3.75 (t, 2H, HN—CH$_2$CH$_2$N),

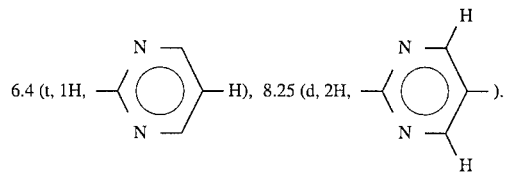

2 basic groups: 99.1%.

EXAMPLE 11:

1-(p-fluorophenyl)-4-[N-[2-(N'-(2-pyrimidinyl)-N'-methyl-amino)ethyl]-N-methylamino]-1-butanone ethyleneketal dihydrochloride To a solution of the compound in Example 10 (16.6 g, 0.1 mole) in 300 ml of acetonitrile, γ-chloro-p-fluorobutyrophenone ethyleneketal (29.4 g, 0.12 mole), K$_2$CO$_3$ (41.4 g, 0.3 mole) and a catalytic amount of KI were sucessively added. The mixture was refluxed for 24 hours. The reaction course was monitored by chromatography on F$_{254}$ silica gel using chloroform-methanol (8:2) as the eluant. The reaction mixture was allowed to become temperate, the organic salts were filtered and the solvent was evaporated giving 42.6 g of a crude product which was then purified by column chromatography (silica gel, eluant Cl$_3$CH and Cl$_3$CH/MeOH 95:5). 17.7 g (Yield, 47.3%) of chromatographically pure product in the form of an oil were obtained.

IR (film) v:2940, 1590, 1410, 1390, 1220 cm$^{-1}$.

¹H—NMR (CDCl₃) δ:

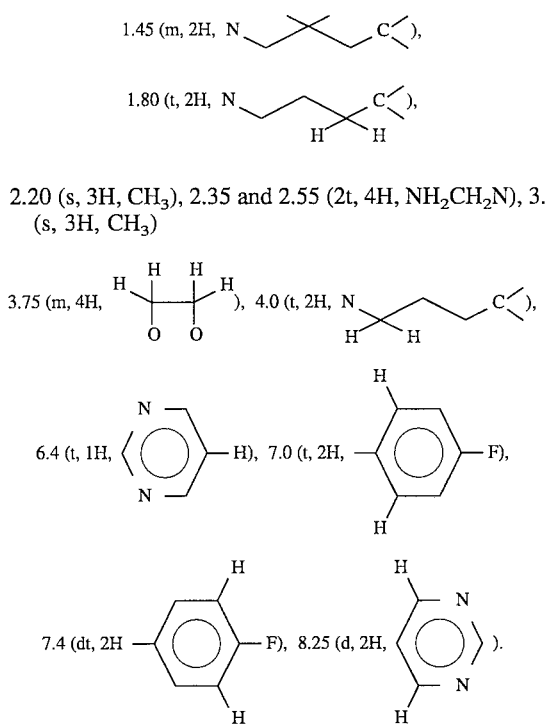

2.20 (s, 3H, CH₃), 2.35 and 2.55 (2t, 4H, NH₂CH₂N), 3.1 (s, 3H, CH₃)

-continued 6.80 (t, 1H, [pyrimidinyl—H]), 7.22 (acid protons), 7.40 (t, 2H, [phenyl—F]), 8.1 (dd, 2H, [phenyl—F]), 8.50 (d, 2H, [pyrimidinyl]).

Melting point: 208°–212° C.

Elemental analysis for $C_{18}H_{23}FN_4O \cdot 2H_2SO_4$: (found) C 41.11 H 5.10 N 10.79 S 11.93; (calculated) C 41.06 H 5.13 N 10.60 S 12.18.

EXAMPLE 12:

1-(p-fluorophenyl)-4-[N-[2-(N'-(2-pyrimidinyl)-N'-methyl-amino)ethyl]-N-methylamino]-1-butanone disulphate The compound in Example 11 (18.7 g, 0.5 mole) was dissolved in absolute ethanol (150 ml) and 20 ml of 6M HCl were added, and the mixture was maintained at 60°–70° C. for 2 h (hydrolysis course was monitored by TLC). The ethanol was next evaporated to dryness, and the crude product obtained was dissolved in water (50 ml), alkalized strongly using 2M NaOH and extracted with chloroform (2×50 ml). The organic phases were combined, dried over anhydrous Na₂SO₄, filtered and evaporated to dryness. The oil formed was dissolved in acetone (100 ml) and acidified with 2M sulphuric acid giving 8.2 g (Yield, 31.2%) of chromatographically pure product in the form of a crystalline white solid.

IR (KBr) ν: 3440, 2960, 1690, 1630, 1220 c⁻¹.

¹H—NMR (DMSO) δ:

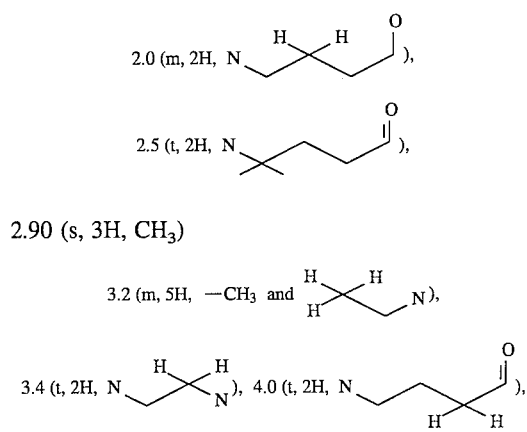

2.90 (s, 3H, CH₃)

EXAMPLE 13:

1-(p-fluorophenyl)-4-[N-[2-(N'- (2-pyrimidinyl) N'-methyl-amino)ethyl]-N-methylamino]-1-butanol disulphate A mixture of the compound in Example 12 (10.52 g, 0.02 mole) and sodium borohydride (1.51 g, 0.04 mole) in absolute ethanol (250 ml) was allowed to react at room temperature under stirring for 24 h. The mixture was treated with ethanol 6M HCl (50 ml) and refluxed for 30 min. After removal of the solvent in vacuo the residue obtained was treated with 2M NaOH (200 ml) and extracted with chloroform (3×200 ml). The organic phases were combined, washed with water (200 ml), dried over anhydrous Na₂SO₄ and concetracted in vacuo. The resin so obtained was dissolved in acetone and treated with H₂SO₄. A chromatographically pure crystalline white solid precipitated to yield 2 g (18.9%).

IR (KBr) ν: 3420, 2960, 1690, 1640, 1520, 1220 cm⁻¹.

¹H—NMR (D₂O) δ:

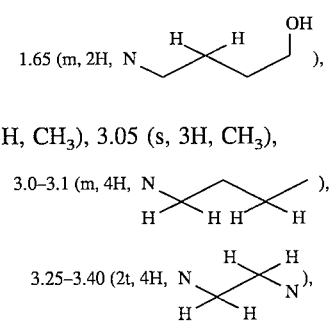

2.75 (s, 3H, CH₃), 3.05 (s, 3H, CH₃),

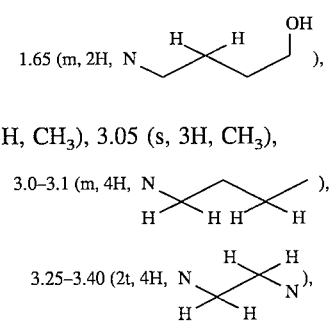

3.9–4.05 (m, 2h, CH—OH), 6.75 (dd, 1H,

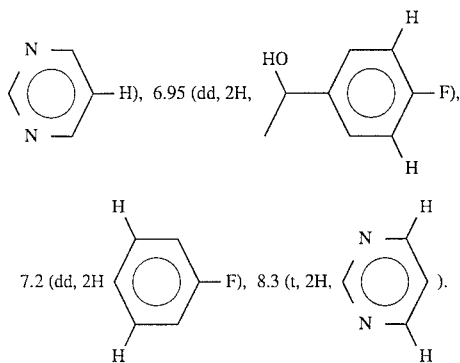

), 6.95 (dd, 2H, 7.2 (dd, 2H

F), 8.3 (t, 2H,

).

Melting point: 179°–181° C.

Elemental analysis for $C_{18}H_{25}FN_4O \cdot 2H_2SO_4$: (found) C 40.68 H 5.35 N 10.47 S 12.15; (calculated) C 40.90 H 5.53 N 0.60 S 12.12.

We claim:

1. (Amended) N,N,N'N'-tetrasubstituted-1,2-ethanediamine compounds of the general formula (I):

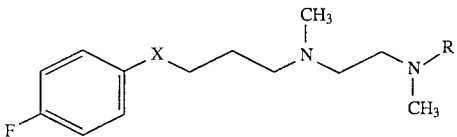

wherein X is a carbonyl hydroxymethylene or p-fluorophenyl-methylene group, and R is a benzyl group optionally substituted in p-position with a halogen, or R is a 2-pyrimidinyl group, with the proviso that simultaneously X may not be p-fluoropheny-methylene and R may not be an unsubstituted benzyl group, and pharmaceutically acceptable additions salts thereof.

2. A compound according to claim 1, wherein R is an unsubstituted benzyl group or 2 benzyl group substituted in the p-position with fluorine.

3. The compound according to claim 1, which is 1-(p-fluorophenyl)-4-(N-(2-(N'-(p-fluorobenzyl)-N'-methyl-amino)ethyl)-N-methylamino )-1-butanone and or the dihydrochloride salt thereof.

4. A compound according to claim 2, wherein R is a benzyl group substituted in the p-position with fluorine.

5. The compound according to claim 3, which is the dihydrochloride salt thereof.

6. A compound according to claim 1, which is selected from the group consisting of 1-Benzyl-1,4-dimethyl-ethylenediamine; 1,4-Dimethyl-1-(p-fluorobenzyl) ethylenediamine; 4-[N-(2-(N'-benzyl ,N'-methylamino) ethyl) -N-methylamino]-1-(p-fluorophenyl)-1-butanone ethyleneketal dihydrochloride; 1-(p-fluorophenyl)-4-[N-(2-(N'-(p-fluorobenzyl)-N'methylamino)ethyl)-N-methylamino]-1-butanone ethyleneketal dihydrochloride; 4-[N-(2-(N'-benzyl, N'methylamino) ethyl)-N-methylamino]-1-(p-fluorophenyl)-1-butanone dihydrochloride; 4-[N-(2-(N'-benzyl,N'-methylamino)ethyl)-N-methylamino]-1-(p-fluorophenyl)-1-butanol dihydorchloride; 1-(p-fluorophenyl) -4- [N-(2-(N'-(p-fluorobenzyl)-N'-methylamino)ethyl)-N-methylamino]-1-butanone dihydrochloride; N-(4,4-bis (p-fluorophenyl butyl)-N,N'-dimethyl-N'-(p-fluorobenzyl)-1,2-ethanediamine dihydrochloride; 1,4-Dimethyl-1-(2 -pyrimidinyl) ethylenediamine; 1-(p-fluorophenyl)-4-[N-[2-(N'-(2-pyrimidinyl)-N'-methyl-amino) ethyl]-N-methylamino]-1-butanone ethyleneketal dihydrochloride; 1-(p-fluorophenyl)-4-[N-(2-pyrimidinyl)-N'-methylamino) ethyl]-N-methylamino]-1-butanone disulphate; and 1-(p-fluorophenyl) -4-[N-[2-N'-(2-pyrimidinyl)-N'-methyl-amino)ethyl]-N-methylamino]-1-butanol disulphate or pharmaceutically acceptable salts thereof.

7. A pharmaceutical composition comprising at least one compound of claim 1, optionally in combination with pharmaceutically acceptable carriers and/or adjuvants.

8. A method for treating sigma receptor-related nervous system diseases which comprises administering a compound of the general formula (I):

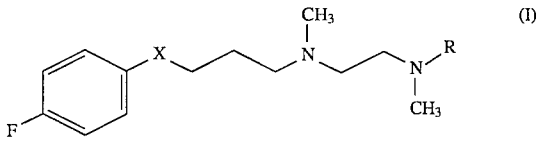

wherein X is a carbonyl, hydroxymethylene or p-fluorophenylmethylene group, and R is a benzyl group optionally substituted in p-position with a halogen, or R is a 2-pyrimidinyl group, with the proviso that simultaneously X may not be p-fluorophenyl-methylene and R may not be an unsubstituted benzyl group, and pharmaceutically acceptable additions salts thereof.

* * * * *